United States Patent [19]

Westley

[11] 4,168,272
[45] Sep. 18, 1979

[54] HOMOLOGS OF LASALOCID A

[75] Inventor: John Westley, Mountain Lakes, N.J.

[73] Assignee: Hoffmann-La Roche Inc., Nutley, N.J.

[21] Appl. No.: 810,123

[22] Filed: Jun. 27, 1977

Related U.S. Application Data

[63] Continuation of Ser. No. 645,970, Jan. 2, 1976, abandoned, which is a continuation of Ser. No. 457,296, Apr. 2, 1974, abandoned.

[51] Int. Cl.² ............................................. C07D 309/06
[52] U.S. Cl. .............................. 260/345.7 R; 424/283
[58] Field of Search ................................. 260/345.7 R

[56] References Cited

U.S. PATENT DOCUMENTS

| | | | |
|---|---|---|---|
| 3,715,372 | 2/1973 | Stempel et al. | 260/345.7 R |
| 3,719,753 | 3/1973 | Berger | 260/345.7 R |

OTHER PUBLICATIONS

Berger et al., J. Amer. Chem. Soc., 73, 5295 (1951).
Chiang et al., Science Journal, 196, 1441 (1977).

*Primary Examiner*—Nicky Chan
*Attorney, Agent, or Firm*—Jon S. Saxe; Bernard S. Leon; Frank P. Hoffman

[57] ABSTRACT

Homologs of antibiotic Lasalocid A and their pharmaceutically acceptable salts are produced by a known species of Streptomyces. The homologs exhibit coccidiostatic and antibacterial activity and thus are useful as coccidiostats and antibacterial agents.

5 Claims, No Drawings

HOMOLOGS OF LASALOCID A

This is a continuation of application Ser. No. 645,970 filed Jan. 2, 1976 now abandoned which in turn is a continuation of 457,296 filed Apr. 2, 1974 now abandoned.

BRIEF DESCRIPTION OF THE INVENTION

This invention relates to new antibiotics and to methods for their production by fermentation, their isolation and purification and their use as coccidiostatic agents and antibacterial agents.

The microorganism producing the antibiotics useful in this invention is a Streptomyces organism isolated from a sample of soil collected at Hyde Park, Mass. Lyophilized tubes of the culture bearing the laboratory designation X-537 were deposited with the United States Department of Agriculture, Agricultural Research Service, Northern Utilization Research and Development Division, Peoria, Ill. The culture, given identification number NRRL 3382 by the Agricultural Research Service, has been made available to the public through NRRL. The culture is also available to the public from the International Center of Information in collaboration with W.H.O. in Belgium.

The antibiotic material, heretofore identified as antibiotic X-537A (Lasalocid A), upon laboratory analysis has been found to be 6-{7(R)-[5(S)-ethyl-5-(5(R)-ethyltetrahydro-5-hydroxy-6(S)-methyl-2H-pyran-2(R)-yl)-tetrahydro-3(S)-methyl-2(S)-furyl]-4(S)-hydroxy-3(R),5(S)-dimethyl-6-oxononyl}2,3-cresotic acid, i.e., a compound of the formula

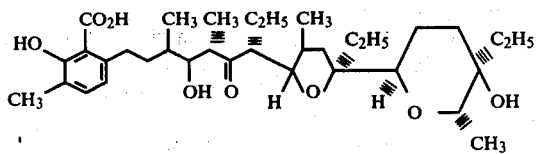

As indicated above, the present invention relates to homologs of antibiotic Lasalocid A and their pharmaceutically acceptable salts. The specific homologs to which the invention relates are compounds of the formula

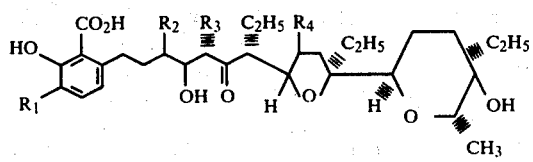

wherein $R_1$, $R_2$, $R_3$ and $R_4$ are selected from the group consisting of methyl and ethyl, provided that only one of $R_1$–$R_4$ is ethyl and three of $R_1$–$R_4$ are methyl.

More specifically, the Lasalocid homologs of the present invention are compounds of the following formulas and nomenclature:

Lasalocid B:

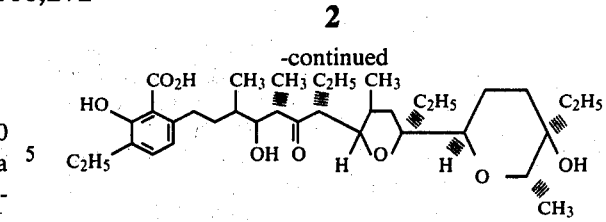

6-{7(R)-[5(S)-ethyl-5-(5(R)-ethyltetrahydro-5-hydroxy-6(S)-methyl-2H-pyran-2(R)-yl)-tetrahydro-3(S)-methyl-2(S)-furanyl]-4(S)-hydroxy-3(R), 5(S)-dimethyl-6-oxononyl}2-hydroxy-3-ethylbenzoic acid.

Lasalocid C:

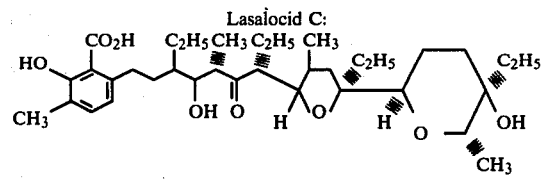

6-{7(R)-[5(S)-ethyl-5-(5(R)-ethyltetrahydro-5-hydroxy-6(S)-methyl-2H-pyran-2(R)-yl)-tetrahydro-3(S)-methyl-2(S)-furyl]-3(R)-ethyl-4(S)-hydroxy-5(S)-methyl-6-oxononyl}-2,3-cresotic acid.

Lasalocid D:

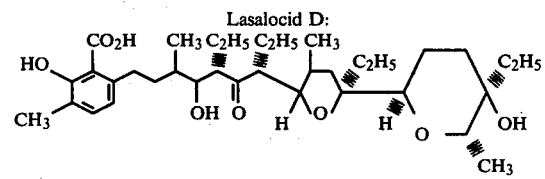

6-{7(R)-[5(S)-ethyl-5-(5(R)-ethyltetrahydro-5-hydroxy-6(S)-methyl-2H-pyran-2(R)-yl)-tetrahydro-3(S)-methyl-2(S)-furyl]-5(S)-ethyl-4(S)-hydroxy-3(R)-methyl-6-oxononyl}2,3-cresotic acid.

Lasalocid E:

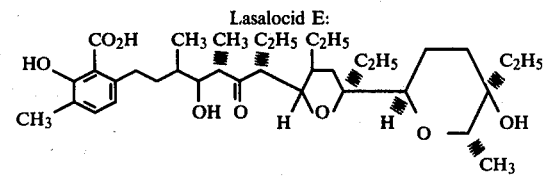

6-{7(R)-[5(S)-ethyl-5-(5(R)-ethyltetrahydro-5-hydroxy-6(S)-methyl-2H-pyran-2(R)-yl)tetrahydro-3(S)-ethyl-2(S)-furyl]-4(S)-hydroxy-3(R),5(S)-dimethyl-6-oxononyl}2,3-cresotic acid.

The homologs are prepared by the fermentation of Streptomyces X-537 under aerobic submerged conditions, with the pH of the fermentation broth adjusted to about neutral, i.e., about 6.5 to 7.5. The medium utilized contains a nitrogen source, such as yeast, a yeast derived product, corn meal, bean meal and the like, with soybean meal being the most preferred; and a carbohydrate source, such as sugar, molasses and the like, with brown sugar being the most preferred. The fermentation is carried out at slightly elevated temperatures, i.e., between about 25° and 35° C., with the preferred incubation temperature being about 28° C. After an incubation of about 4 to 6 days, the fermentation broth is filtered and the antibiotics recovered by extraction.

After the fermentation is complete, a variety of procedures can be employed for the isolation and purification of the homologs. Suitable isolation and purification procedures include solvent extraction techniques, such as batchwise extraction or counter-current continuous flow liquid-liquid extraction columns and gel permeation chromatography in a non-aqueous system.

The pharmaceutically acceptable salts of the homologs can be prepared by conventional means. These salts are prepared from the free acid form of the antibiotic or its derivatives by methods well known in the art, for example, by washing the free acid in solution with a suitable base or salt. Examples of such pharmaceutically acceptable basic substances capable of forming salts for the purpose of the present invention include alkali metal bases such as sodium hydroxide, potassium hydroxide, lithium hydroxide and the like; alkaline earth metal bases such as calcium hydroxide, barium hydroxide and the like; and ammonium hydroxide. Alkali metal or alkaline earth metal salts suitable for forming pharmaceutically acceptable salts can include anions such as carbonates, bicarbonates and sulfates.

The relative antibiotic activity of the lasalocid homologs B, C, D and E in In vitro testing against the organism Bacillus TA was calculated by comparing a pure antibiotic lasalocid A sodium salt and the four homologs using the cup-plate agar diffusion technique. The calculated values of the five components were based on an activity of 100 for lasalocid A base and are shown in the table below

| Compound | Calculated in vitro activity vs Bacillus TA |
|---|---|
| Lasalocid A | 100 |
| Lasalocid Homolog B | 90 |
| Lasalocid Homolog C | 180 |
| Lasalocid Homolog D | 160 |
| Lasalocid Homolog E | 170 |

The Coccidiostatic compositions of this invention containing as the active ingredient, homologs of antibiotic Lasalocid A, or their pharmaceutically acceptable salts or the dried unfiltered broth are prepared by mixing the active ingredient with an inert ingredient. The inert ingredient can comprise a feedstuff, extender materials and the like. By the term "inert ingredient" is meant a material which does not function as an antiparasitic agent, e.g., a coccidiostat, is inactive with respect to the active ingredient and which may be safely ingested by the animals to be treated, and thus, such inert material is one which is inactive for the purpose of the present invention.

The active ingredient when orally administered to coccidiosis susceptible domestic fowl, particularly turkeys and chickens, as a component of feed, effectively controls the disease by either preventing it or curing it after it occurs. Furthermore, the treated fowl either maintain their weight or actually gain weight when compared to controls. Thus, the compositions of this invention not only control coccidiosis, but also aid in improving the efficiency of conversion of feed to weight gains.

The actual concentration of the active ingredient in animal feed can, of course, be adjusted to the individual needs and may vary over a wide range. The limiting criteria of the concentration are that the minimum concentration is such that a sufficient amount of active ingredient is provided to effect the desired control of coccidiosis and the maximum concentration is such that the amount of composition ingested does not result in any untoward or undesirable side effects.

Thus, for example, a feed premix or complete feed contains sufficient active ingredient to provide from about 0.006% to about 0.03% by weight of the daily feed consumption. Preferably, about 0.015% to 0.03% by weight is used. Generally, about 0.015% of the active ingredient is sufficient for the purpose of controlling and combatting coccidiosis. Amounts greater than 0.015%, while being effective against coccidiosis, do not generally show improved results over 0.015% and in some cases may adversely affect the growth, feed efficiency and mortality.

Even though amounts over 0.03% are efficacious for combatting coccidiosis, this amount is the preferred upper range because of economics, i.e., the cost per unit of effectiveness is lowest within this range. Amounts lower than 0.006% are not effective for combating coccidiosis. Preferred is a lower limit of 0.015% because this insures efficaciousness. The most preferred amount, i.e., about 0.015% by weight of the poultry daily feed consumption is particularly efficacious since it achieves maximum effect with minimum dose.

The optimum dose level will, of course, vary with the size of the animal. When using the antibiotics in accordance with the invention for treating or preventing coccidiosis, it can be first compounded or blended with a feed ingredient or carrier to become a feed additive premix, a feed concentrate, or a feed additive supplement. A feed additive, concentrate or premix is an article intended to be diluted to produce a complete feed, i.e., an article intended to be administered as a sole ration. A feed additive supplement is an article intended for consumption by an animal directly or which can be further diluted to produce a complete feed or can be ingested and used as a supplement to other rations. Feed additive supplements, concentrates and premixes contain a relatively large percentage of coccidiostats, i.e., the active ingredient to a suitable carrier and mixing in a manner to give substantially uniform dispersion of the coccidiostat in the carrier. Suitable carriers are solids that are inert with respect to the active ingredient and which may safely be ingested by the animals to be treated. Typical of such carriers are commercial poultry feeds, ground cereal grains, grain by-products, plant protein concentrates (soy, peanuts, etc.) fermentation by-products, salt, limestone, inorganic compounds, and the like or admixtures thereof. Liquid dispersions can be prepared by using water or vegetable oil preferably including a surface active agent, emulsifying agent, and the like, in the liquid dispersion such as ethylene diamine tetracetic acid, etc. and solubilizers. Any suitable carrier or extender material can function as the inert ingredient in the solid form of the antiparasitic agent provided that it is inert to the active material and is non-toxic insofar as the animal to which it is to be administered is concerned.

The active ingredient may be blended into a mash, pellet, or any desired configuration with the inert carrier or extender solid material by any convenient technique. For example, compositions can be formed by finely grinding or pulverizing the active ingredient and the inert ingredient using any commercially available grinder or pulverizer with or without the feed material being present. If the feed material is not present when the grinding or pulverizing is effected, the resultant material can be distributed, in accordance with the present invention, in any conveniently available feed material. Typical poultry feeds which can be medicated with the active ingredient of this invention can contain several ingredients, for example, they can contain high energy grain products such as corn, wheat, wheat red dog flour, milo, oatmeal, or the like; medium and low energy grain products, such as oats, barley, wheat flour, middlings, standard middlings or the like; stabilized fats; vegetable protein such as soybean meal, corn gluten meal, peanut meal, or the like; animal protein such as fish meal, fish solubles, meat scraps or the like; UGF (unidentified growth factor) sources and other B-vitamin carriers such as dried milk products, dried brewers yeast, distillers dried solubles, fermentation solubles, or the like; dehydrated alfalfa meal; and various special additives such as additional riboflavin, vitamin $B_{12}$, calcium pantothenate, niacin, choline, vitamin K and vitamin E or the like, as well as stabilized vitamin A, vitamin $D_3$ (D-activated animal sterols); calcium and phosphorus supplements such as dicalcium phosphate, steamed bone meal, defluorinated phosphate, limestone, or the like; iodized salt, manganese sulfate, zinc carbonate, an antibiotic feed supplement; methionine or its hydroxy analog, and an antioxidant.

As is evident from the above, the coccidiostat compositions are intended for oral ingestion. They can be added to the normal feed supply of the treated animal or can be administered by other procedures, such as incorporating the same in a tablet, pill or bolus and supplying it forcibly to the animal. The administration of the active ingredient must be considered in terms of the specific animal under the husbandry practices encountered.

The inventive compounds and their use as Coccidiostats are illustrated by the following examples:

EXAMPLE 1

Preparation of Lasalocid Homologs B,C,D, and E

The streptomyces organism was grown in aerated submerged culture in the shaken flasks. The pH of the broth was adjusted by the addition of KOH solution to 6.5–7.5, then the broth was sterilized. A tank fermentation was used hwerein a 5–10% inoculum consisting of 3-day-old submerged growth from aerated bottles was used in the tank. The medium contained 2% soybean flour, 2% brown sugar, 0.1% $K_2HPO_4$ and 0.5% cornsteep liquor. The fermentation was carried out at 28° C. under positive air pressure, with air-flows of 5–10 cu. ft. of air per minute per 40- to 80-gallon liquid charge. The broth was harvested after 4 to 6 days fermentation, filtered, and the antibiotic was recovered by extraction. The extraction was carried out as follows:

204 liters of broth were filtered and the wet filter cake was suspended in 100 liters of butyl acetate and the mixture was stirred overnight, at room temperature. The mixture was then filtered and the water layer was separated and discarded. The butyl acetate solution, assaying 30 million Bacillus E units, was concentrated in vacuo to 3 liters, washed with 10% sodium carbonate solution, and dried with anhydrous sodium sulfate.

On further concentration to 300 ml. and dilution with 350 ml. of petroleum ether (B.P. 50°–60° C.), 41 g. of solid material, assaying 25 million Bacillus E. units separated. This solid material was then extracted in a Soxhlet apparatus with 4 liters petroleum ether (B.P. 50°–60° C.) for 40 hours. The extract was taken to dryness in vacuo, the crystalline residue suspended in petroleum ether and filtered. Repeated crystallization gave mother liquor enriched in homologs.

EXAMPLE 2

Isolation of Lasalocid Homologs B, C, D, E

A portion (equal to 22 g solids) of the final mother liquors from the large scale preparation of Example 1 was chromotographed in a 200 tube (each 80 ml capacity) counter current distribution apparatus. The sample was dissolved in 160 ml of the mixed phases (heptane-ethyl acetate-methanol-water, 27:18:18:2) and the solution placed in the first two tubes. After 380 transfers, the following fractions were pooled and the solids recovered after evaporation identified as:

A. Mixture of lasalocid homologs B,C,D and E
B. Lasalocid A
C. Isolasalocid A

Fraction A was dissolved in 20 ml of the mixed phases of the solvent system heptane, ethyl acetate, ethanol, water and glacial acetic acid (10:5:9:3:1) and subjected to chromotography on a 500 tube counter current distribution apparatus. After 2800 transfers, approximately 200 mg. each of lasalocids B,C,D and E were separated and upon analysis had the following melting points:

Lasalocid B—MP. 85°–87° C.
Lasalocid C—MP. 97°–100° C.
Lasalocid D—MP 102°–104° C.
Lasalocid E—MP. 90° C.

EXAMPLE 3

Sodium Salt of Homolog Lasalocid E

Approximately 100 mg. of lasalocid E was dissolved in methylene chloride and treated with a saturated solution of aqueous sodium carbonate. The solvent layer was concentrated with hexane to give 104 mg. of the crystalline lasalocid E sodium salt (mp. 182°–182.5° C.).

EXAMPLE 4

This example illustrates the utilization of a mixture of antibiotic coccidiostats in an animal feed. A medicated poultry feed intended as a starter feed for broilers is prepared by blending 0.015% by weight and 0.006% by weight of a mixture of Lasalocids B & C (50/50) and Lasalocids D and E (50/50) in a basic poultry ration consisting of:

| Ingredients | Weight Units |
| --- | --- |
| Corn meal, No. 2, yellow ground | 1.123 pounds/ton |
| Stabilized grease or vegetable oil | 60 pounds/ton |
| Soybean oil meal (low fiber content 50% protein | 480 pounds/ton |
| Corn gluten meal | 50 pounds/ton |
| Fish meal, antioxidant treated, 60% protein | 30 pounds/ton |
| Fish solubles, dried basis | 10 pounds/ton |
| Meat and bone scraps, 50% protein | 140 pounds/ton |
| Corn distillers dried solubles | 50 pounds/ton |
| Alfalfa meal, 17% protein 100,000 A/lb. | 30 pounds/ton |
| Manganese sulfate, feed grade | 0.75 pounds/ton |
| Zinc carbonate or oxide | 0.25 pounds/ton |
| Riboflavin | 3 grams |
| Vitamin $B_{12}$ | 6 mg. |
| Calcium pantothenate | 5 grams |
| Niacin | 30 grams |
| Stabilized Vitamin A | 6,000,000 USP units |
| Vitamin $D_3$ | 650,000 I.C. |
| Vitamin E acetate | 5,000 I.C. |
| Vitamin E (menadione sodium bisulfite) | 2 grams |
| DL-methionine or hydroxy analog | 1 pounds/ton |
| Antioxidant (ethoxyquin or butylated hydroxy toluene) | 0.25 pounds/ton |

*Eimeria tenella* infection in laboratory chickens

Test method.—This test utilizes ten chickens per drug group. Ten chickens are employed as a weight control and ten chickens as an infected control. The drug is given 48 hours in advance of the infection. One gm. of the test drug is mixed in a mechanical mixer with a sufficient amount of chicken feed to result in the desired dosage. The infection consists of approximately 200,000 oocysts given orally by pipette. The tests lasts for eleven days and then the surviving birds are autopsied and examined for gross lesions in the ceca. The test birds are rated according to the number of survivors and the number of lesions. The results are expressed as average degree of infection (A.D.I.). An average degree of infection of less than 1.5 is considered significant.

As can be seen from the data in the table below, the mixture of antibiotics is effective at the dosages illustrated for the treatment of coccidiosis.

| Compound | | Dosage in feed | Average Degree of Infection | Percent Mortality |
|---|---|---|---|---|
| Uninfected Untreated Control | | None | 0.0 | 0 |
| Infected Untreated Control | | None | 2.6-2.8 | 10-20 |
| Lasalocid Homolog B | Mixture in a 1:1 Ratio | 0.015 | 1.0 | 0 |
| Lasalocid Homolog C | | 0.006 | 1.2 | 0 |
| Lasalocid Homolog D | Mixture in a 1:1 Ratio | 0.015 | 0.0 | 0 |
| Lasalocid Homolog E | | 0.006 | 1.2 | 0 |

EXAMPLE 5

This example illustrates the utilization of a single antibiotic coccidiostat in an animal feed. A medicated poultry feed intended as a starter feed for broilers is prepared as in Example 4. About 0.01% by weight of Lasalocid D is blended in a basic poultry ration as used in Example 4. The test method employed for *Eimeria tenella* in Example 4 was followed as can be seen from the data in the table the antibiotic is effective at the preferred dosage illustrated for the treatment of coccidiosis.

| Compound | Dosage in Feed | Average Degree of Infection | Percent Mortality |
|---|---|---|---|
| Uninfected Untreated Control | None | 0.0 | 0 |
| Infected Untreated Control | None | 3.0 | 20 |
| Lasalocid Homolog D | 0.01 | 0.5 | 0 |

I claim:

1. A compound of the formula:

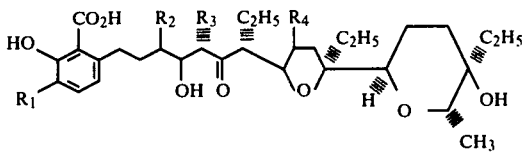

wherein $R_1$, $R_2$, $R_3$, and $R_4$ are selected from the group consisting of methyl and ethyl, provided that only one of $R_1$–$R_4$ is ethyl, or the pharmaceutically acceptable salts thereof.

2. The compound of claim 1, wherein $R_1$ is ethyl and $R_2$, $R_3$ and $R_4$ are methyl.

3. The compound of claim 1, wherein $R_2$ is ethyl and $R_1$, $R_3$ and $R_4$ are methyl.

4. The compound of claim 1, wherein $R_3$ is ethyl and $R_1$, $R_2$ and $R_4$ are methyl.

5. The compound of claim 1, wherein $R_4$ is ethyl and $R_1$, $R_2$ and $R_3$ are methyl.

* * * * *